US00PP19467P2

(12) United States Plant Patent
Stemkens

(10) Patent No.: US PP19,467 P2
(45) Date of Patent: Nov. 18, 2008

(54) ***VERBENA* PLANT NAMED 'CARMALI'**

(50) Latin Name: *Verbena×hybrida*
Varietal Denomination: Carmali

(75) Inventor: Henricus G. W. Stemkens, Andijk (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/002,379

(22) Filed: Dec. 17, 2007

(51) Int. Cl.
*A01H 5/00* (2006.01)

(52) U.S. Cl. ..... Plt./308

(58) Field of Classification Search ..... Plt./308
See application file for complete search history.

(56) References Cited

U.S. PATENT DOCUMENTS

PP17,714 P2 * 5/2007 Stemkens ..... Plt./308

* cited by examiner

*Primary Examiner*—Wendy C. Haas
(74) *Attorney, Agent, or Firm*—S. Matthew Edwards

(57) ABSTRACT

A new *Verbena* plant, characterized particularly as to novelty, by its rose flowers, which appear earlier on the plant, and a growing habit that is spreading.

1 Drawing Sheet

Latin name of the genus and species of the plant claimed: *Verbena×hybrida.*
Varietal denomination: 'Carmali'.

BACKGROUND OF THE NEW PLANT

The present invention comprises a new distinct cultivar of *Verbena,* botanically known as *Verbena×hybrida.*

The new *Verbena×hybrida* is a product of a planned breeding program conducted in Enkhuizen, Netherlands.

A new *Verbena* plant particularly distinguished by its rose flowers, early flowering, and a habit that is first semi-erect and later spreading.

The new cultivar is propagated from cuttings resulting from the cross of 'E1108-1' and 'B0852-8.' 'E1108-1' is a blue flowering *Verbena* having a spreading habit. 'E1108-1' is not commercially available and is not known by any synonyms. 'B0852-8' is a pink flowering *Verbena* having a spreading habit. 'B0852-8' is not commercially available and is not known by any synonyms. Neither 'E1108' or 'B0852-8' has been patented.

As a result of this cross the present cultivar was created in 2003 in Enkhuizen, Netherlands and has been repeatedly asexually reproduced by cuttings in Enkhuizen and Sarrians, France over a three year period. It has been found to retain its distinctive characteristics through successive propagations, and this novelty appears to be firmly fixed.

This new *Verbena* plant is an annual in most climatic zones in the US, except in zones 9 and 10, where it is a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

BOTANICAL DESCRIPTION OF THE PLANT

The following detailed descriptions set forth the distinctive characteristics of this new *Verbena.* The data which defines these characteristics were collected from asexual reproductions carried out in Enkhuizen. The plant history was taken on 14 week old plants, blossomed under natural light in a greenhouse.

Color readings were taken in the greenhouse under ambient light. Color references are primarily to The R.H.S. Colour Chart of The Royal Horticultural Society of London.

TABLE 1

Differences between the new cultivar 'Carmali', its parents and the most resembling variety

| | 'Carmali' | 'E1108-1' | 'B0852-8' | 'Carpin' (U.S. Plant Patent No. 17,714) |
|---|---|---|---|---|
| Flower color | Rose | Blue | Pink | Pink |
| Earliness | Early | Very early | Late | Early |
| Plant size | Medium | Compact | Big | Big |
| Seed set | No | No | Much | No |

The plant:

*Classification.*—Botanical: *Verbena×hybrida.*
*Parentage.*—Female parent: 'E1108-1'. Pollen parent: 'B0852-8'.
*Growth habit.*—Spreading.
*Plant height.*—14–20 cm.
*Spreading area of plant.*—35–65 cm.
*Growth rate.*—Hanging and vigorous.
*Strength.*—Resistant to hot and cool weather.
*Branching character.*—Freely branching and lateral branching at every node.
*Blooming period.*—From April until November.

The stem:

*Diameter.*—2.5–3 mm.
*Shape.*—Tetragonal.
*Anthocyan pigmentation.*—Absent.
*Color.*—146B.

*Length of internode.*—20 mm in the middle of summer and under high light conditions and 40 mm in the early spring and autumn and under low light conditions.

*Pubescence.*—Pubescence is present.

The foliage:

*Phyllotaxis.*—Opposite.

*Shape of blade.*—Broadly ovate.

*Texture.*—Uppder side: Pubescent. Lower side: Pubescent.

*Venation.*—Pinnate.

*Leaf margin.*—Pinnatipartite.

*Leaf base.*—Shortly attenuate.

*Leaf apex.*—Acute.

*Length.*—25–40 mm.

*Width.*—18–30 mm.

*Depth of incision.*—3–8 mm.

*Color.*—Upper side: 137B. Lower side: 137D.

*Pubescence.*—Some pubescence is present.

*Length of leaf stem.*—5–12 mm.

*Petiole surface structure.*—Slightly pubescent.

The bud:

*Peduncle length.*—30 mm in the middle of the summer and 60 mm in the early spring and autumn.

*Size.*—Diameter: 2 mm. Length: 8–12 mm.

*Shape.*—Elongated and ovate.

*Color.*—137B.

*Sepals.*—Color: 137B. Form: Upright. Number: 5, fused. Size: 5 mm. Shape: Elongated.

The flower:

*Facing direction: Upward.*

*Outward curvature of petal.*—Slightly curved.

*Diameter.*—20 mm.

*Height.*—18–20 mm.

*Borne.*—In a cluster.

*Form.*—Salverform; sessile on terminal spikes.

*Cluster.*—Spike.

*Colour.*—N66A.

*Eye.*—A very small (1 mm) whitish eye (155C) is present. Three out of the five petals typically exhibit this whitish coloration.

*Overlapping of petals.*—Separate.

*Number of petals.*—Gamopetalous, 5 lobed.

*Shape of the petals.*—Each petal is heart shaped at the apex and grown together at the base.

*Petal margin.*—Entire.

*Petal surface texture.*—Smooth.

*Size of the petal.*—Length: 6–8 mm. Width: 6–8 mm.

*Spike.*—Length: 25–35 mm. Diameter: 30–45 mm.

*Calyx length.*—8–10 mm.

*Anthocyan pigmentation of calyx limb.*—Absent.

*Color of the calyx.*—137A.

*Number of flowers per spike.*—20–25.

*Fragrance.*—A very light fragrance occurs.

*Lastingness of the bloom.*—New florets continue to open in one spike over a period of 14 days.

*Lastingness of the flower.*—On the plant 3 days, off the plant 1.5 hours.

Reproductive organs:

*Androecium.*—Stamens quantity: 4. Anther shape: Ovoid. Anther lenght: 1 mm. Anther color: 144D. Pollen amount: Scarce pollen. Pollen color: 145D.

*Gynoecium.*—Pistils quantity: 1. Pistil length: 18–22 mm. Stigma shape: Bi-lobed. Stigma color: 144C. Style length: 14–18 mm. Style color: 144D. Ovary color: 144C.

Seed development: No seed set has been observed to date.

Roots:

*Type of roots.*—Fibrous. Roots start to grow on every part of the stem that contacts the soil, so not only at the nodes.

Physiological and ecological characteristics: No resistance to diseases commonly known in *Verbena* has been observed to date.

*Good resistance to heat.*—−2–38 degrees Celsius.

In the claims:

1. A new and distinct variety of *Verbena* plant named 'Carmali,' as substantially illustrated and described herein.

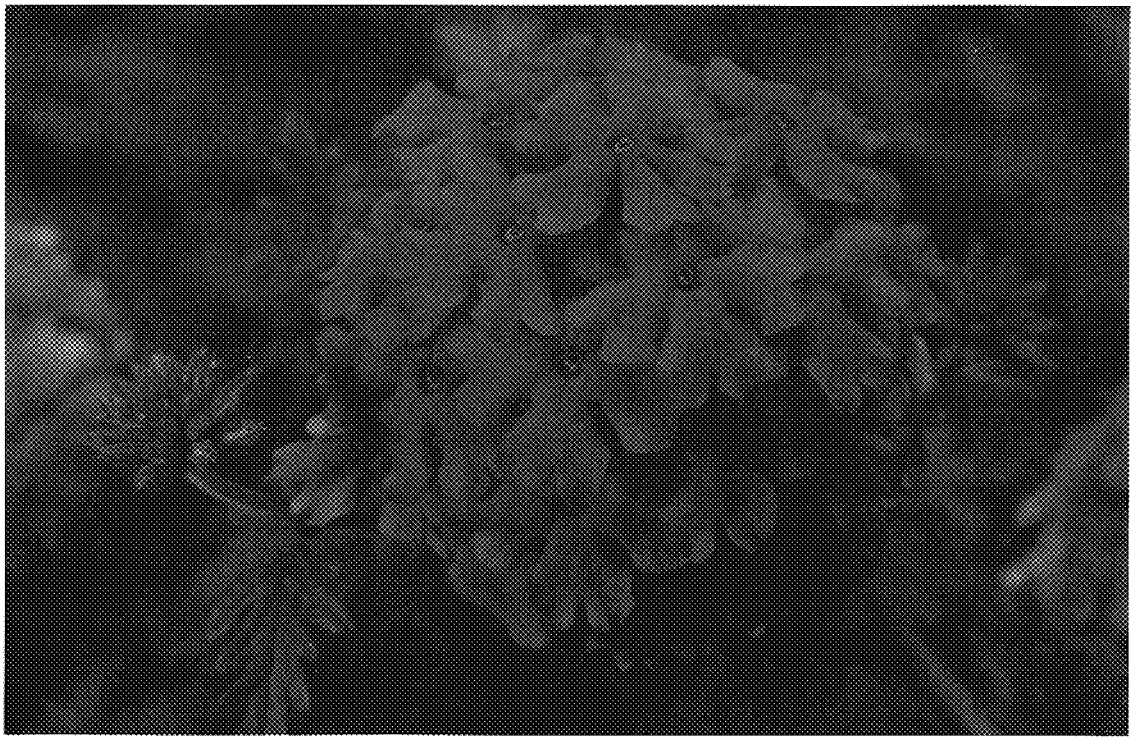

* * * * *